(12) United States Patent
Ogasawara et al.

(10) Patent No.: US 8,663,421 B2
(45) Date of Patent: Mar. 4, 2014

(54) APPARATUS AND METHOD OF MANUFACTURING ABSORBENT ARTICLE

(75) Inventors: Yoshikazu Ogasawara, Kagawa (JP); Noriaki Ito, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 17 days.

(21) Appl. No.: 13/133,761

(22) PCT Filed: Dec. 2, 2009

(86) PCT No.: PCT/JP2009/070253
§ 371 (c)(1),
(2), (4) Date: Aug. 5, 2011

(87) PCT Pub. No.: WO2010/071022
PCT Pub. Date: Jun. 24, 2010

(65) Prior Publication Data
US 2012/0090774 A1    Apr. 19, 2012

(30) Foreign Application Priority Data
Dec. 18, 2008  (JP) .................................. 2008-322778

(51) Int. Cl.
B29C 43/24    (2006.01)
(52) U.S. Cl.
USPC .......................................... 156/301; 156/297
(58) Field of Classification Search
USPC .............. 156/301, 519, 582, 297; 100/155 R, 100/158 R, 176
See application file for complete search history.

(56) References Cited

U.S. PATENT DOCUMENTS

| 6,905,572 B2 * | 6/2005 | Yu .................................. 156/582 |
| 2003/0221785 A1 | 12/2003 | Yu |
| 2005/0072512 A1 | 4/2005 | Shiomi et al. |

FOREIGN PATENT DOCUMENTS

| EP | 1 535 591 A1 | 6/2005 |
| JP | 2004-121831 A | 4/2004 |
| JP | 2004121831 A | 4/2004 |
| JP | 2005-075639 A | 3/2005 |
| JP | 2005075639 A | 3/2005 |
| JP | 2005-245789 A | 9/2005 |
| JP | 2005-298193 A | 10/2005 |
| JP | 2007-301196 A | 11/2007 |
| JP | 2007301196 A | 11/2007 |
| JP | 2005245789 A | 9/2009 |

OTHER PUBLICATIONS

International Search Report for PCT/JP2009/070253 mailed Mar. 2, 2010.

(Continued)

*Primary Examiner* — Christopher Schatz
*Assistant Examiner* — John Blades
(74) *Attorney, Agent, or Firm* — Lowe Hauptman & Ham, LLP

(57) ABSTRACT

An apparatus that manufactures an absorbent article includes a rotating member that rotates in a state where the rotating member is opposing one face of a continuous sheet that is moving, the rotating member having an arcuate retaining surface that retains a work, the rotating member causing the work to be moved to a position where the work is nipped between the one face and the arcuate retaining surface by rotating in a state where the work is retained on the arcuate retaining surface; and a pressing member that bonds a continuous sheet and a work together by coming into contact with another face of the continuous sheet when the work reaches the position and pressing the continuous sheet towards the arcuate retaining surface.

4 Claims, 6 Drawing Sheets

(56) References Cited

OTHER PUBLICATIONS

Supplementary European Search Report dated Jun. 7, 2013 for Eurasian patent application.
Office Action dated Jul. 2, 2013 for corresponding Colombian patent application.
Philippine Office Action dated Jun. 23, 2013.
Office Action as issued on Apr. 16, 2013 in corresponding Eurasian Patent Application.
Office Action issued in Chinese Application No. 200980151489.X dated Dec. 21, 2012, 5 pages.
Eurasian Office Action dated Aug. 13, 2013 and translation for corresponding Application No. 201100952.

* cited by examiner

APPARATUS AND METHOD OF MANUFACTURING ABSORBENT ARTICLE

RELATED APPLICATIONS

The present application is a National Phase of International Application Number PCT/JP2009/070253, filed Dec. 2, 2009, which claims priority from Japanese Patent Application No. 2008-322778, filed Dec. 18, 2008.

TECHNICAL FIELD

The present invention relates to an apparatus and a method of manufacturing of an absorbent article.

BACKGROUND ART

In a production line of absorbent articles such as disposable diapers and sanitary napkins, there are cases in which a work and a continuous sheet are bonded together.

As a manufacturing apparatus of an absorbent article for performing such bonding process, an apparatus is known which includes a rotating member that rotates in a state where the rotating member is opposing one face of a continuous sheet that is moving, the rotating member having an arcuate retaining surface that retains a work, the rotating member causing the work to be moved to a position where the work is nipped between the one face and the arcuate retaining surface by rotating in a state where the work is retained on the arcuate retaining surface; and a pressing member that bonds the continuous sheet and the work together by coming into contact with another face of the continuous sheet when the work reaches the position and pressing the continuous sheet towards the arcuate retaining surface (see JP-A-2004-121831 and JP-A-2005-298193).

DISCLOSURE OF INVENTION

Problems to be Solved by the Invention

In the related art, when bonding a work and a continuous sheet together using a manufacturing apparatus of an absorbent article having the rotational member and a pressing member described above, there are cases where the attaching was not properly performed. Accordingly, due to the improper attaching, there are cases where one of them peels off from the other. Therefore, there is a need for a manufacturing apparatus of an absorbent article that can achieve appropriate bonding.

The present invention has been made in view of such a problem and its object is to appropriately bond a continuous sheet and a work together.

Means for Solving the Problems

In order to achieve the object described above, the main aspect of the present invention is:

an apparatus that manufactures an absorbent article including:

a rotating member that rotates in a state where the rotating member is opposing one face of a continuous sheet that is moving, the rotating member having an arcuate retaining surface that retains a work, the rotating member causing the work to be moved to a position where the work is nipped between the one face and the arcuate retaining surface by rotating in a state where the work is retained on the arcuate retaining surface; and a pressing member that bonds the continuous sheet and the work together by coming into contact with another face of the continuous sheet when the work reaches the position and pressing the continuous sheet towards the arcuate retaining surface, the pressing member being a roller that is freely rotatable about a central axis, a central axis direction of the roller intersecting with a central axis direction of a center of circle of the arcuate retaining surface when the roller comes into contact with the other face, a line of intersection of an outer surface of the roller and a virtual plane containing the central axis of the roller being an arcuate curved line, a diameter of the roller at a central section in the central axis direction of the roller being smaller than a diameter of the roller at an end section of the central axis of the roller.

Other aspects of the invention will be elucidated from the description and accompanying drawings.

Advantageous Effects of the Invention

According to an aspect of the invention, a continuous sheet and a work can be appropriately bonded together.

LIST OF REFERENCE NUMERALS

Figure 1:
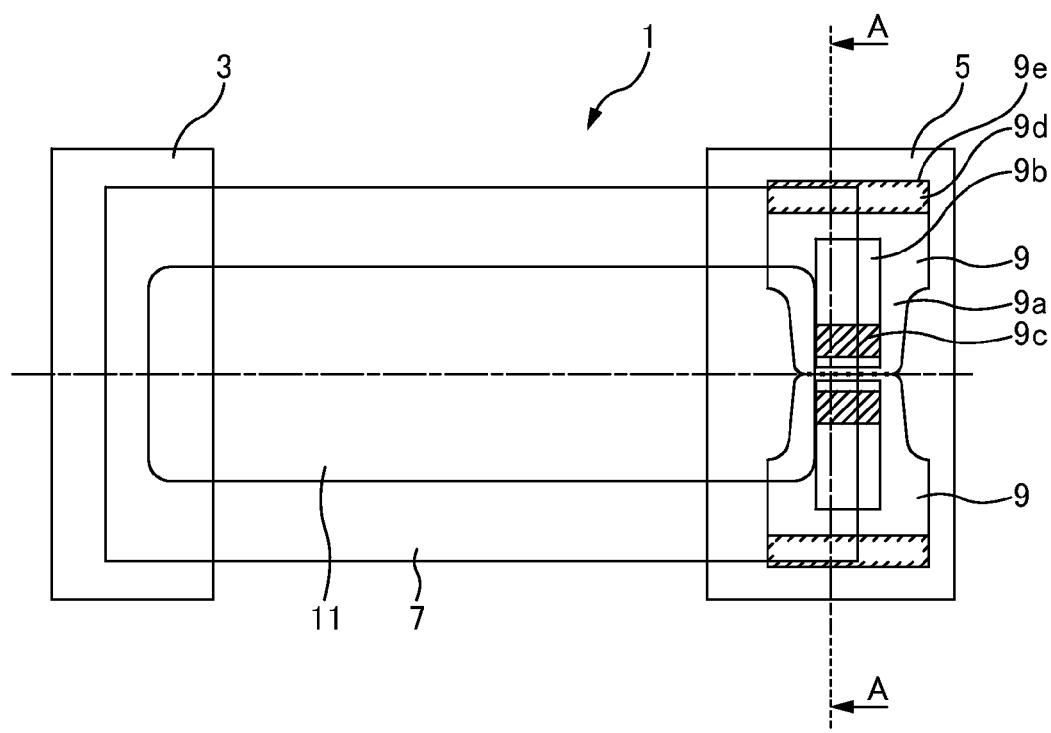
FIG. 1 is a diagram illustrating a diaper 1 in a developed configuration.

1 diaper (absorbent article), 3 stomach-side belt member,
5 back-side belt member, 5a skin-side nonwoven fabric,
7 absorbent main body, 9 fastening tape member (work),
9a sheet, 9b reinforcement material, 9c securing section,
9d adhering section, 9e end, 11 absorbent body,
13 front-face sheet member, 15 reverse-face sheet member,
17 liquid permeable sheet, 19 elastic thread,
21 fastening tape base material,
23 back-side belt base material (continuous sheet),
23a front face (one face), 23b reverse face (other face),
23c vacant portion, 31 manufacturing apparatus, 33 endless belt,
35 lower roll (rotating member), 35a rotation axis,
35b peripheral surface (arcuate retaining surface),
37 upper roll, 37a blade, 39 hammer roll unit,
41 hammer roll (pressing member), 41a outer surface,
41b central axis, 41c end section, 43 supporting roller, 43a central axis, 43b inner wall, 44 bearing member, 45 collar,
47 suction section, 51 retaining pallet, 51a rotation axis,
51b arcuate retaining surface, L line of intersection,
G gap, C central section, E end section

MODE FOR CARRYING OUT THE INVENTION

At least the following matters will be disclosed in the present specification and accompanying drawings.

An apparatus that manufactures an absorbent article includes:

a rotating member that rotates in a state where the rotating member is opposing one face of a continuous sheet that is moving, the rotating member having an arcuate retaining surface that retains a work, the rotating member causing the work to be moved to a position where the work is nipped between the one face and the arcuate retaining surface by rotating in a state where the work is retained on the arcuate retaining surface; and a pressing member that bonds the continuous sheet and the work together by coming into contact with another face of the continuous sheet when the work reaches the position and pressing the continuous sheet towards the arcuate retaining surface, the pressing member being a roller that is freely rotatable about a central axis, a central axis direction of the roller intersecting with a central axis direction of a center of circle of the arcuate retaining surface when the roller comes into contact with the other face, a line of intersection of an outer surface of the roller and a virtual plane containing the central axis of the roller being an arcuate curved line, a diameter of the roller at a central section in the central axis direction of the roller being smaller than a diameter of the roller at an end section of the central axis of the roller.

With such manufacturing apparatus of absorbent article, a continuous sheet and a work can be appropriately bonded together.

It is preferable that, in such apparatus that manufactures an absorbent article, the work is provided with an adhesive section that adheres with the continuous sheet when bonded together with the continuous sheet, and the pressing member comes into contact with a portion on the other face of the continuous sheet where the adhering section does not exist on the one face side and presses the continuous sheet towards the arcuate retaining surface.

With such manufacturing apparatus of absorbent article, production of creases can be suppressed when bonding the continuous sheet and the work together.

It is preferable that, in such apparatus that manufactures an absorbent article, the pressing member comes into contact with a portion on the other face of the continuous sheet where the work does not exist on the one face side and presses the continuous sheet against the arcuate retaining surface.

With such manufacturing apparatus of absorbent article, production of creases can be further suppressed when bonding the continuous sheet and the work together.

It is preferable that, in such apparatus that manufactures an absorbent article, the pressing member is a roller that is configured to be freely slidable in the central axis direction.

With such manufacturing apparatus of absorbent article, an impact force that the pressing member receives from the rotating member can be appropriately mitigated.

Further, a method of manufacturing an absorbent article includes:

moving a work, with a rotating member that rotates in a state where the rotating member is opposing one face of a continuous sheet that is moving and that has an arcuate retaining surface that retains a work, to a position where the work is nipped between the one face and the arcuate retaining surface by rotating in a state where the work is retained on the arcuate retaining surface; and bonding the continuous sheet and the work together by a pressing member coming into contact with another face of the continuous sheet when the work reaches the position and pressing the continuous sheet towards the arcuate retaining surface, the pressing member being a roller that is freely rotatable about a central axis, a central axis direction of the roller intersecting with a central axis direction of a center of circle of the arcuate retaining surface when the roller comes into contact with the other face, a line of intersection of an outer surface of the roller and a virtual plane containing the central axis of the roller being an arcuate curved line, a diameter of the roller at a central section in the central axis direction of the roller being smaller than a diameter of the roller at an end section of the central axis of the roller.

With such manufacturing method of absorbent article, a continuous sheet and a work can be appropriately bonded together.

Present Embodiment

Figure 2:
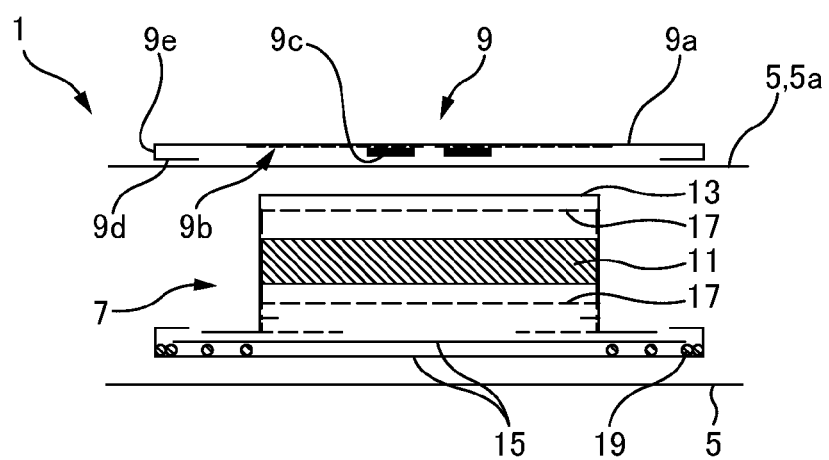
FIG. 2 is a view taken in a direction of arrows A-A in FIG. 1.
Figure 3A:
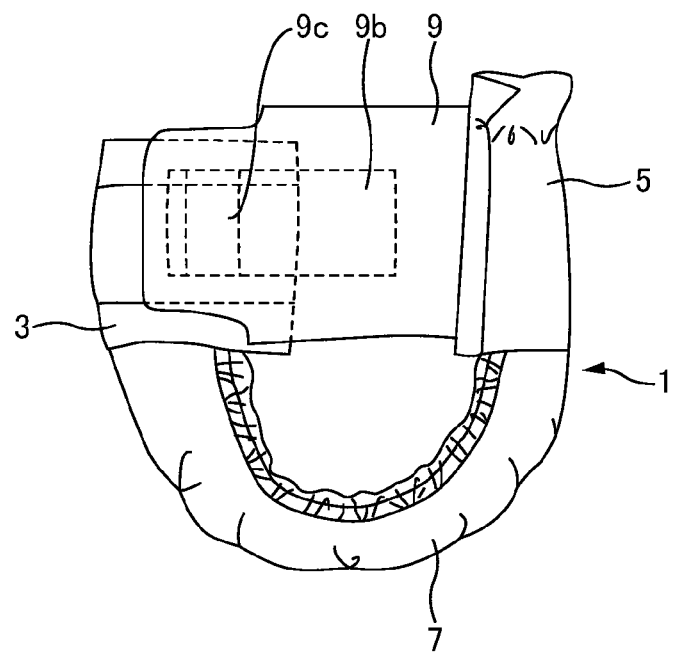
FIG. 3A is a diagram illustrating the diaper 1 in a worn configuration (first diagram).
Figure 3B:
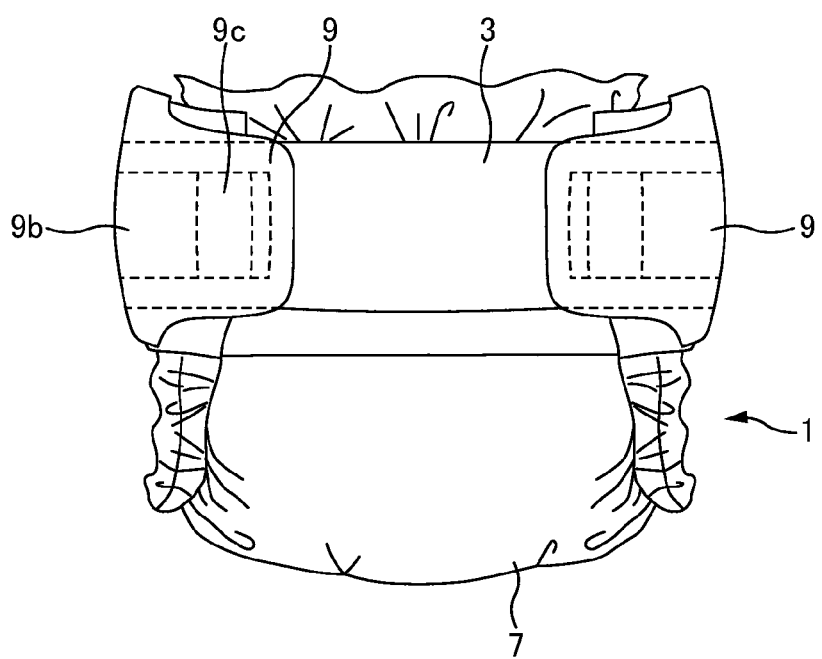
FIG. 3B is a diagram illustrating the diaper 1 in a worn configuration (second diagram).

An absorbent article manufacturing apparatus 31 of the present embodiment is, for example, used in a production line of disposable diapers. Before making an explanation of the above-mentioned apparatus 31, a configuration of a disposable diaper (hereinafter simply referred to as a diaper 1) will be first described with reference to FIGS. 1 to 3B. FIG. 1 is a diagram illustrating the diaper 1 in a developed configuration. FIG. 2 is a view taken in a direction of arrows A-A in FIG. 1. FIGS. 3A and 3B are diagrams illustrating the diaper 1 in a worn configuration. In the description below, in a thickness direction of the diaper, a side that comes into contact with a wearer's body will be referred to as a skin face side and a side opposite thereto will be referred to as a reverse face side.

The diaper 1 of the present embodiment is a so-called open type which is folded from a developed configuration (see FIG. 1) to a worn configuration (see FIGS. 3A and 3B) in use. The diaper is provided with a stomach-side belt member 3 having a belt-like shape and located on a stomach side of the wearer, a back-side belt member 5 located on a back side, an absorbent main body 7 that is placed against the crotch and absorbs bodily fluid such as urine and a fastening tape member 9 (commonly referred to as a flap) that joins the back-side belt member and the stomach-side belt member.

As shown in FIG. 1, an external shape of the diaper 1 in a developed configuration has a substantially H-shape when seen in a thickness direction. That is to say, the stomach-side belt member 3 and the back-side belt member 5 are arranged in parallel with a space between each other and between them is the absorbent main body 7 with either end sections in the longitudinal direction being bridged across. From such a state, the absorbent main body 7 is folded in half with a central section in its longitudinal direction being a folding position, and the stomach-side belt member 3 and the back-side belt member 5 opposing each other in such two-fold state are joined into a ring shape via a fastening tape member 9. At this point, the fastening tape member 9 extends from the back side to the stomach side and is fastened at a position near of the wearer's flank. By joining the stomach-side belt member 3 and the back-side belt member 5, the diaper 1 will be in a worn configuration as shown in FIGS. 3A and 3B. In a state of the worn configuration, the stomach-side belt member 3, the back-side belt member 5 and the fastening tape member 9 covers around the wearer's waist.

The absorbent main body 7 is a layered sheet that is rectangular when seen in a thickness direction and includes an absorbent body 11 that absorbs bodily fluid such as urine, a front face sheet member 13 that covers the absorbent body 11 from a side of the wearer's skin and a reverse face sheet member 15 that covers the absorbent body 11 from an opposite side of the front face sheet member 13 and that also serves an exterior of the diaper 1. With the absorbent body 11 being sandwiched between the reverse face sheet member 15 and the front face sheet member 13, the reverse face sheet member 15 and the front face sheet member 13 are bonded together in a frame-like manner at a section spreading outwardly from four sides of the absorbent body 11, and thus the absorbent body 11 is fabricated. Also, as shown in FIG. 2, a liquid permeable sheet 17 such as tissue paper is provided between the front face sheet member 13 and the absorbent body 11 and between the reverse face sheet member 15 and the absorbent body 11. Further, an elastic thread 19 for forming a gathering section is attached to the reverse face sheet member 15 at each width-direction end section thereof and along a longitudinal direction thereof.

The stomach-side belt member 3 and the back-side belt member 5 are each made of a flexible sheet such as a nonwoven fabric and shaped in a substantially rectangular shape when seen in the thickness direction. Here, the belt members are each made of nonwoven fabric in two-ply. The belt members are each bonded to a corresponding longitudinal-direction end section of the absorbent main body 7 and are secured in such a manner that they intersect with the absorbent main body 7. It is to be noted that the longitudinal-direction end sections of the absorbent main body 7 are sandwiched and secured between the two-ply nonwoven fabrics.

The fastening tape member 9 is bonded to the skin face-side surface of the back-side belt member 5 at a position slightly towards the center from its longitudinal-direction end. On the other hand, a target tape (not shown) is bonded to the reverse face-side surface of the stomach-side belt member 3 from one end to the other end in the longitudinal direction. This target tape is a nonwoven fabric provided with a surface on which a securing section 9c, which is to be described later, of the fastening tape member 9 is secured.

The fastening tape member 9 is made of a flexible sheet 9a such as a nonwoven fabric and provided one each at line symmetrical positions about a central line of the diaper (a virtual line passing through a center in an intersecting direction). Before the diaper is worn, each of the fastening tape members 9 in a pair is in a closed state by being folded towards the center of the diaper, and opened outwardly when worn. At a tip end of a surface of the sheet 9a that comes to a skin-face side in the opened state, the securing section 9c such as a hook material of a hook and loop fastener is bonded via a reinforcement material 9b. On the other hand, an end section at a fixed end side of each of the fastening tape members 9 is folded over in a crest-like manner and bonded to the back-side belt member 5 with an adhesive agent (i.e., an adhering section 9d is formed at an end section at the fixed end side.)

Further, in the present embodiment, the pair of fastening tape members 9 is not split but rather joined in a single sheet-like manner at the time of shipment of the diaper 1. Specifically, at the time of shipment, a single sheet of nonwoven fabric that constitutes the pair of fastening tape members 9 is attached and a perforation serving as a splitting line is formed at the center (the center in the intersecting direction) of the nonwoven fabric. The wearer splits the nonwoven fabric along the splitting line when wearing the diaper. Accordingly, the pair of fastening tape members 9 is made with the nonwoven fabric.

Such diaper 1 is completed by joining various constituent components to a base material of the diaper 1 that is traveling continuously in the production line. The manufacturing apparatus 31 of the present embodiment carries out one of the processes.

Figure 4:
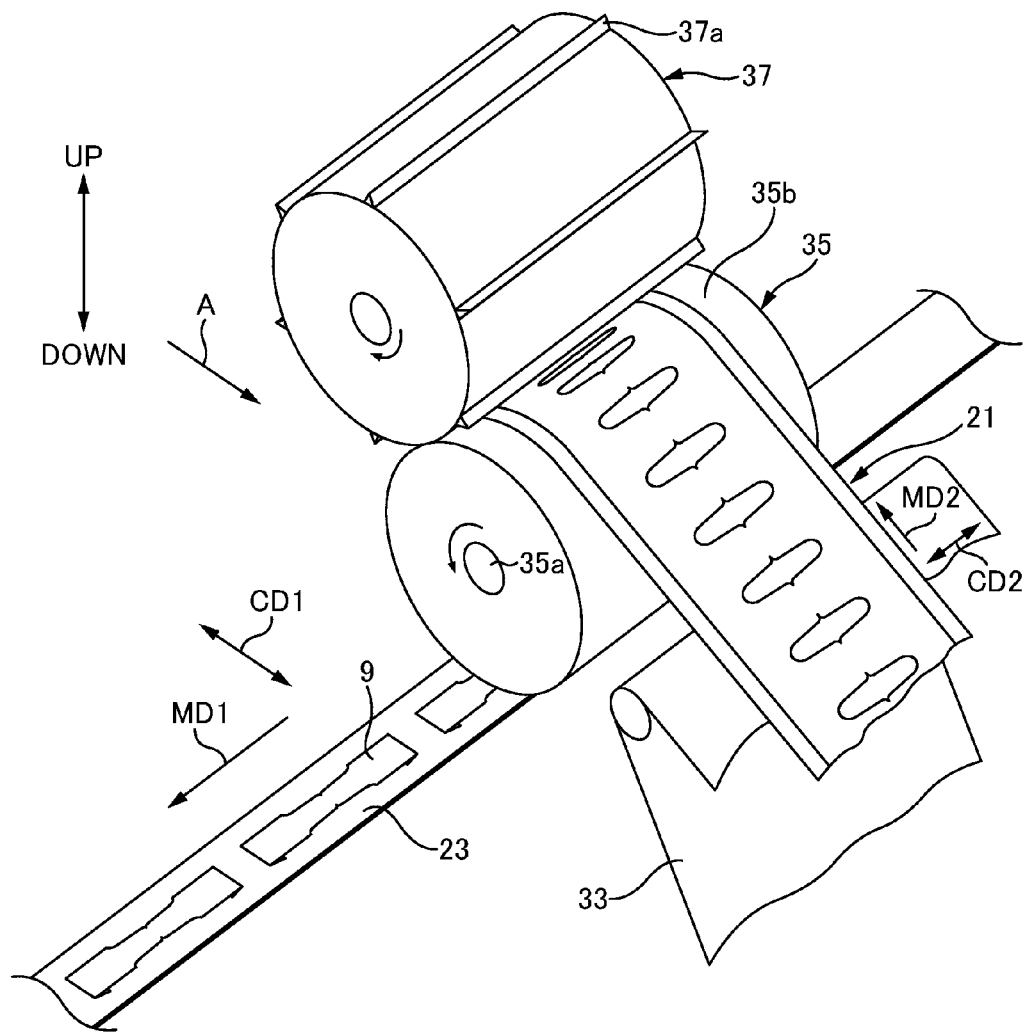
FIG. 4 is a schematic diagram illustrating a part of a manufacturing apparatus 31.

Explaining about the process carried out by the manufacturing apparatus 31, the manufacturing apparatus 31 fabricates a fastening tape member 9 by cutting a fastening tape base material 21 which is a base member of the above-mentioned fastening tape member 9 and in which a plurality of fastening tape members 9 are connected in a line (see FIG. 4). Then, the fabricated fastening tape member 9 (corresponds to a work) is bonded to a back-side belt base material 23 (corresponds to a continuous sheet, see FIG. 4) which is a base member of the above-mentioned back-side belt member 5 (specifically, a nonwoven fabric 5a on a skin face side of the back-side belt member 5 which is a two-ply nonwoven fabric) and in which a plurality of back-side belt members 5 (the nonwoven fabric 5a on the skin side) are connected in a line.

FIG. 4 is a schematic diagram illustrating a part of the manufacturing apparatus 31. In FIG. 4, an endless belt 33 as well as a lower roll 35 and an upper roll 37 that are exemplary rotating members are illustrated as constituent members of the manufacturing apparatus 31.

The endless belt 33 is for supplying a fastening tape base material 21 to the lower roll 35. This endless belt 33 supplies the fastening tape base material 21 placed thereon to the lower roll 35 by rotating (transports in an MD2-direction as shown in FIG. 4).

The upper roll 37 and the lower roll 35 are cylindrical members that are close to each other and that rotate in mutually opposite directions. By cooperating, the upper roll 37 and the lower roll 35 have a function of fabricating the fastening tape member 9 by cutting the fastening tape base material 21. It is to be noted that the upper roll 37 is located upwardly of the lower roll 35, and respective directions of rotation are substantially parallel to each other and also intersect with the MD2-direction (lies along the CD2-direction).

When cutting the fastening tape base material 21, the lower roll 35 serves as a supporting table for an object to be cut and the upper roll 37 serves as a cutting member. By rotating, the lower roll 35 sends the fastening tape base material 21 to the upper roll 37 (to be more specific, between the upper roll 37 and the lower roll 35) in a state where the fastening tape base material 21 supplied by the endless belt 33 is retained on a peripheral surface. On the peripheral surface of the upper roll 37, a plurality of blades 37a are provided that extend in a direction along a rotational axis direction of the upper roll 37 and that are arranged at a constant interval in a peripheral direction, and each of the blade 37a that moves due to a rotation of the upper roll 37 cuts the fastening tape base material 21 placed between both rolls when it comes close to the lower roll 35.

Figure 5:
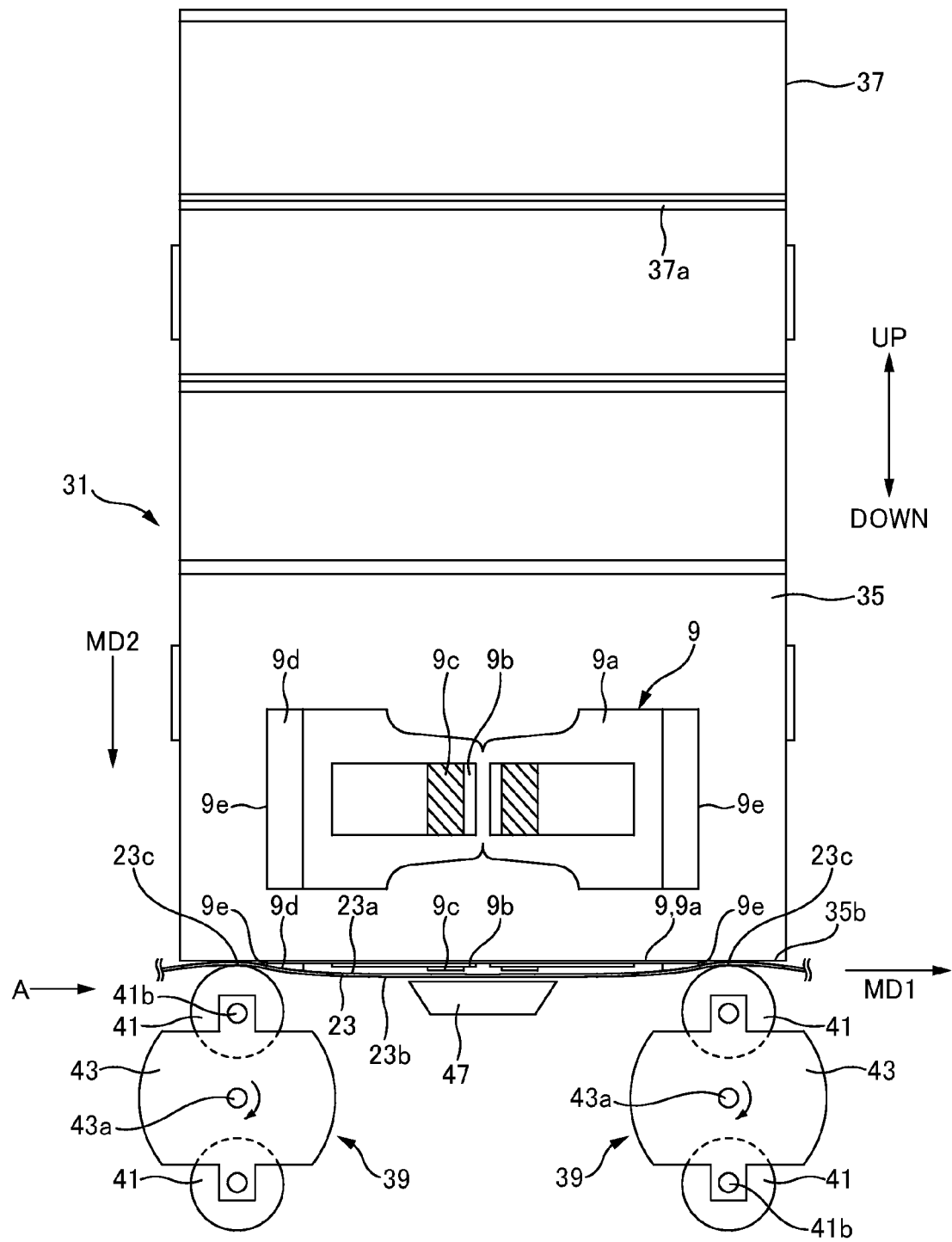
FIG. 5 is a schematic diagram of the manufacturing apparatus 31 of FIG. 4 when seen in direction A.
Figure 6:
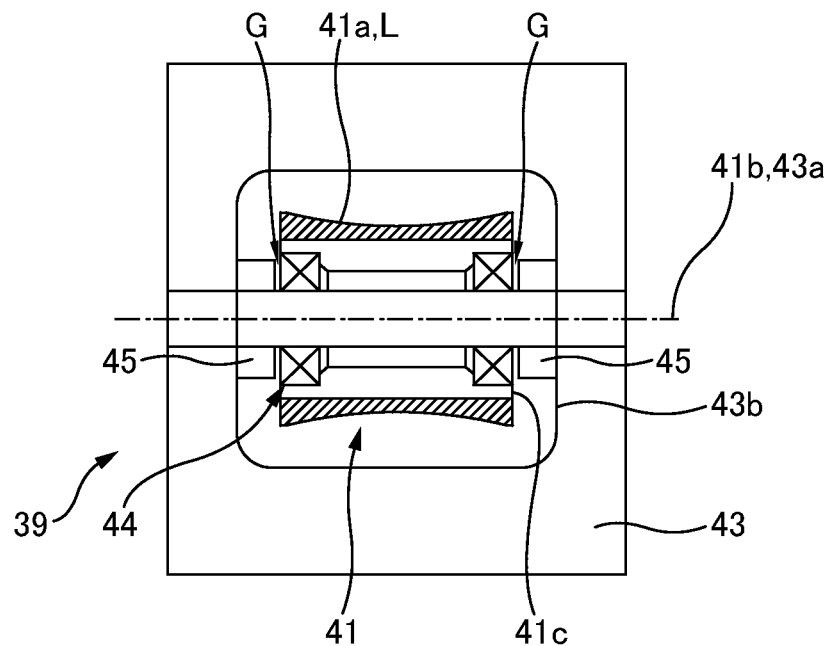
FIG. 6 is a front view of a hammer roll unit 39.
Figure 7:
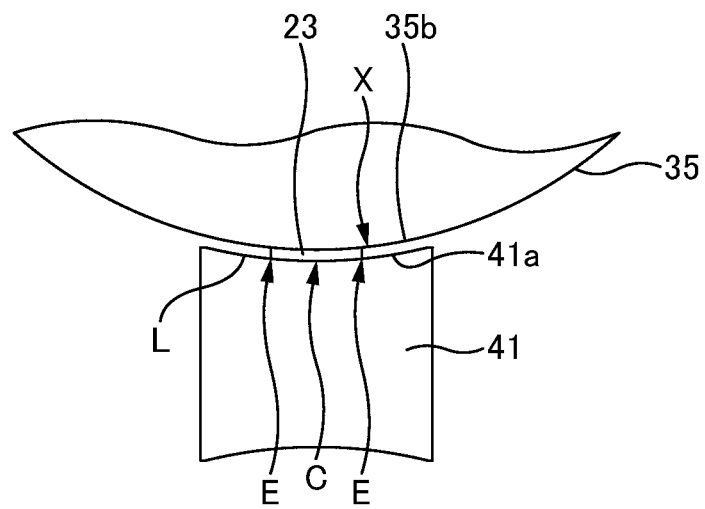
FIG. 7 is a diagram schematically representing a state where the manufacturing apparatus 31 of FIG. 6 is seen in direction A.

FIG. 5 is a schematic diagram of the manufacturing apparatus 31 of FIG. 4 when viewed in direction A. In FIG. 5, in addition to the above-mentioned lower roll 35, a hammer roll unit 39 that has a hammer roll 41, a suction section 47, and the like are illustrated as an exemplary pressing member. FIG. 6 is a front view of the hammer roll unit 39 and FIG. 7 is a diagram schematically representing a state where the manufacturing apparatus 31 of FIG. 6 is viewed in direction A.

In addition to the above-mentioned fastening tape base material cutting function in cooperation with the upper roll 37, the lower roll 35 has a function of moving the fastening tape member 9 to a position directly above the back-side belt base material 23 for bonding the fastening tape member 9 and the back-side belt base material 23 together by rotating the fastening tape member 9 obtained by cutting the fastening tape base material 21 in a state where it is retained on the peripheral surface 35b (corresponds to an arcuate retaining surface for holding the work). The back-side belt base material 23 moves in a moving direction (MD1-direction) (see FIG. 4) by a moving mechanism (not shown). Concerning the positional relationship between the back-side belt base material 23 and the lower roll 35, the lower roll 35 is located at a position higher than the back-side belt base material 23 and rotates in such a manner that the peripheral surface 35b of the lower roll 35 opposes a front face 23a (corresponds to one face) of the back-side belt base material 23 and the rotational axis direction lies along the above-mentioned moving direction (MD1-direction).

In other words, the fastening tape member 9 obtained by cutting the fastening tape base material 21 is retained on the lower roll 35 in a state where its longitudinal direction lies along the rotational axis direction of the lower roll 35. Due to the rotation of the lower roll 35, the fastening tape member 9 gradually moves downwardly (and in the MD2-direction) while being retained on the lower roll 35 (the fastening tape member 9 in motion is shown in FIG. 5). Eventually, the fastening tape 9 comes to a position directly above the back-side belt base material 23, i.e., a position closest to the back-side belt base material 23 (in addition to the fastening tape member 9 in motion, the fastening tape member 9 located at such position is also shown in FIG. 5). At this position, the fastening tape member 9 is nipped between the front face 23a of the back-side belt base material 23 and the peripheral surface 35b of the lower roll 35 (here, "nipped" is intended to include the nipping with two members in contact as well as the nipping with a gap existing between the two members). It is to be noted that, during the above-mentioned movement of the fastening tape member 9, the back-side belt base material 23 continues to move in the MD1-direction.

The hammer roll unit 39 is provided with two hammer rolls 41 and a supporting roller 43 that supports the hammer rolls 41. The hammer rolls 41 and the supporting rollers 43 are located at positions lower than the back-side belt base material 23 in motion.

The hammer roll 41 is a pressing member that comes into contact with a reverse face 23b (corresponds to another face) of the back-side belt base material 23 and presses the back-side belt base material 23 towards the peripheral surface 35b of the lower roll 35. This hammer roll 41 joins the back-side belt base material 23 to the fastening tape member 9 (bonds the back-side belt base material 23 and the fastening tape member 9 together) by pressing the back-side belt base material 23 towards the peripheral surface 35b and moving the back-side belt base material 23 upwardly.

The hammer roll 41 is a roller made of ebonite and a length of the roller in the central axis direction is longer than a maximum diameter of the roller. Further, as shown in FIGS. 6 and 7, a diameter of the roller at a central section in the central axis direction of the roller is smaller than a diameter of the roller at an end section of the central axis of the roller. To be more specific, the diameter of the roller is the smallest at the center in the central axis direction of the roller and the diameter of the roller becomes gradually greater as it approaches the end of the roller in the central axis direction. In other words, a line of intersection L where the outer surface 41a of the roller intersects with an imaginary plane containing the central axis 41b is a curved line. Particularly, in the present embodiment, the line of intersection L is an arcuate (corresponds to a circle with a radius of approximately 12 cm) curved line, and as shown in FIG. 7, a contour of the outer surface 41a of the roller lies along a contour of the peripheral surface 35b of the lower roll 35 having a cylindrical shape.

Also, the hammer roll 41 is located in such a manner that its central axis direction intersects with the central axis direction of a center of circle (i.e., a rotation axis direction of the lower roll 35) of the arcuate retaining surface (peripheral face 35b). In other words, when the roller comes into contact with the reverse face 23b of the back-side belt base material 23, it comes into contact in a state where the central axis direction of the roller intersects with the central axis direction of the center of circle of the peripheral surface 35b (rotational axis direction of the lower roll 35).

Also, the hammer roll 41 is supported by the supporting roller 43 and moves upwardly due to a rotation of the supporting roller 43 and comes into contact with the back-side belt base material 23. In other words, the supporting roller 43 supports the hammer roll 41 at its end sections in a radial direction in such a manner that the central axis direction of the hammer roll 41 lies along the rotational axis direction of the supporting roller 43 and rotates in a clockwise direction in FIG. 5 by receiving a driving force from a drive source which is not shown in the drawings. Then, when the supporting roller 43 rotates in a clockwise direction, the hammer roll 41 performs a revolution motion about the central axis 43a of the supporting roller 43, moves upwardly, and comes into contact with the reverse face 23b of the back-side belt base material Also, as shown in FIG. 6, the hammer roll 41 is supported by the supporting roller 43 via a bearing member 44 such as a bearing and is freely rotatable about the central axis 41b. In other words, the hammer roll 41 is provided on the supporting roller 43 in a freely rotatable manner.

Also, the hammer roll 41 is configured in such a manner that it is freely slidable in the central axis direction. In other words, in the present embodiment, as shown in FIG. 6, a collar 45 is provided between an end section 41c of the hammer roll 41 in the central axis direction and an inner wall 43b of the supporting roller 43 and a gap G (see FIG. 6) is formed between the collar 45 and the end section 41c. In other words, a length of the collar 45 in the central axis direction is made short to such an extent that the gap G is formed.

It is to be noted that in the present embodiment, two hammer rolls 41 are supported by the supporting roller 43 in such a manner that both of them are arranged in point symmetry about the central axis 43a of the supporting roller 43, and when the supporting roller 43 rotates, both hammer rolls 41 come into contact with the back-side belt base material 23 alternately. Further, the manufacturing apparatus 31 of the present embodiment is provided with two hammer roll units 39 each having two hammer rolls 41 and a supporting roller 43, and as shown in FIG. 5, both of the hammer roll units 39 are provided at positions corresponding to either end sections of the lower roll 35 in the rotational axis direction.

Then, the hammer roll 41 bonds the back-side belt base material 23 and the fastening tape member 9 together in the following manner. In other words, as has been described above, due to the rotation of the lower roll 35, the fastening tape member 9 gradually moves downwardly while being retained on the peripheral surface 35b of the lower roll 35, and eventually arrives at a position where it is nipped between the front face 23a of the back-side belt base material 23 and the peripheral surface 35b of the lower roll 35 (for the sake of convenience, hereinafter referred to as a nipped position). (When reaching the nipped position, the fastening tape member 9 is moving in a direction along the central axis direction of the hammer roll 41). Then, as shown in FIG. 5, when the fastening tape member 9 reaches the nipped position, the hammer roll 41 comes into contact with the reverse face 23b of the back-side belt base material 23 (i.e., a rotational speed of the lower roll 35 and a rotational speed of the supporting roller 43 and the like are adjusted in such a manner that the hammer roll 41 can come into contact with reverse face 23b of the back-side belt base material 23 at the time when the fastening tape member 9 reaches the nipped position). It is to be noted that when the hammer roll 41 comes into contact with the back-side belt base material 23, the back-side belt base material 23 is also moving in the MD1-direction, i.e., a direction intersecting with the central axis direction of the hammer roll 41.

When the fastening tape member 9 reaches the above-mentioned nipped position, a bonding surface (adhesive agent is applied here) of the adhesive section 9d of the fastening tape member 9 (a section that adheres with the back-side belt base material 23 when bonded with the back-side belt base material 23) faces downwards and is opposing the front face 23a of the back-side belt base material 23 (see FIG. 5). Then, at such time, when the hammer roll 41 comes into contact with the back-side belt base material 23, the back-side belt base material 23 is pressed towards the peripheral surface 35b and moves upwards, i.e., towards the fastening tape member 9. Then, when the back-side belt base material 23 moves towards the fastening tape member 9, the bonding face of the fastening tape member 9 on which the adhesive agent is applied adheres to the front face 23a of the back-side belt base material 23, and thus the back-side belt base material 23 and the fastening tape member 9 will be bonded together.

When both are bonded together, retention of the fastening tape member 9 by the peripheral surface 35b is released and the fastening tape member 9 moves together with the back-side belt base material 23 in the MD1-direction while being affixed to the front face 23a of the back-side belt base material 23. In other words, in the present embodiment, retention of the fastening tape member 9 is achieved in such a manner that the fastening tape member 9 is sucked via a hole provided in the peripheral surface 35b by a suction mechanism provided in the lower roll 35. Therefore, the retention force becomes weak to such an extent that the retention is released when the back-side belt base material 23 and the fastening tape member 9 are bonded together, and the fastening tape member 9 will be smoothly transferred to the back-side belt base material 23. Also, in order to achieve a more smooth transfer, an ejection mechanism is also provided in the lower roll 35. In other words, when the above-mentioned hole provided in the peripheral surface 35b reaches a zone indicated with a symbol X in FIG. 7 as a result of a rotation of the lower roll 35, a blow (ejection of air) will be produced outwardly through the hole by the above-mentioned ejection mechanism. Then, by an action of the ejected air onto the fastening tape member 9, the fastening tape member 9 will be more smoothly transferred to the back-side belt base material 23.

Also, in the present embodiment, as shown in FIG. 5, the hammer roll 41 is configured to come into contact with a portion on the reverse face 23b of the back-side belt base material 23, specifically the portion where the adhering section 9d (to be more precise, the fastening tape member 9 itself, too) does not exist on the front face 23a side. (Hereinafter referred to as a "vacant portion 23c" for the sake of convenience.) In other words, as illustrated in FIG. 5, the fastening tape member 9 reaches the above-mentioned nipped position while being retained at a center of the peripheral surface 35b of the lower roll 35 in the rotational axis direction and the hammer roll 41 comes into contact at a position (a vacant portion 23c) more to the outer side than the fastening tape member 9 (an end 9e thereof) in the rotational axis direction. That is to say, the hammer roll 41 does not directly press the back-side belt base material 23 against the adhering section 9d (fastening tape member 9) but rather presses a portion adjacent to the vacant portion 23c on the reverse face 23b against the adhering section 9d (fastening tape member 9) by pressing the vacant portion 23c where the fastening tape member 9 does not exist on the front face 23a side.

Also, when the fastening tape member 9 has reached the above-mentioned nipped position, the affixing face as well as the securing section 9c are facing downwards and opposes the front face 23a of the back-side belt base material 23 (see FIG. 5). Then, in order to prevent the securing section 9c from being secured to the back-side belt base material 23 when the hammer roll 41 comes into contact with the reverse face 23b of the back-side belt base material 23 and presses the back-side belt base material 23 towards the peripheral surface 35b, a suction section 47 is provided between the two hammer roll units 39. When the hammer roll 41 comes into contact with the back-side belt base material 23, the suction section 47 sucks the back-side belt base material 23 downwardly (i.e., in a direction in which the back-side belt base material 23 will be separated apart from the securing section 9c). In other words, if the suction section 47 does not exist, when the hammer roll 41 presses the back-side belt base material 23 towards the peripheral surface 35b, the securing section 9c may be stuck to the back-side belt base material 23 due to an upward movement of the back-side belt base material 23, but with the above-mentioned suction being performed by the suction section 47, an occurrence of the above-mentioned problem can be positively avoided.

===Effectiveness of the Absorbent Article Manufacturing Apparatus 31 of the Present Embodiment===

As has been described above, the absorbent article manufacturing apparatus 31 of the present embodiment includes a lower roll 35 that rotates in a state where the lower roll 35 is opposing a front face 23a of a back-side belt base material 23 that is moving, the lower roll 35 having a peripheral surface 35b that retains a fastening tape member 9, the lower roll 35 causing the fastening tape member 9 to be moved to a position where the fastening tape member 9 is nipped between the front face 23a and the peripheral surface 35b by rotating in a state where the fastening tape member 9 is retained on the peripheral surface 35b; and a hammer roll 41 that bonds the back-side belt base material 23 and the fastening tape member 9 together by coming into contact with a reverse face of the back-side belt base material 23 when the fastening tape member 9 reaches the position and pressing the back-side belt base material 23 towards the peripheral surface 35b. The hammer roll 41 is a roller that is freely rotatable about a central axis, a central axis direction of the roller intersects with a central axis direction (rotational axis direction of the lower roll 35) of a center of circle of the peripheral surface 35b when the roller comes into contact with the reverse face 23b, a line of intersection L of an outer surface 41a of the roller and a virtual plane containing the central axis 41b of the roller being an arcuate curved line, and a diameter of the roller at a central section in the central axis direction of the roller is smaller than a diameter of the roller at an end section of the central axis of the roller. Accordingly, the back-side belt base material 23 and the fastening tape member 9 can be appropriately bonded together.

Figure 8:
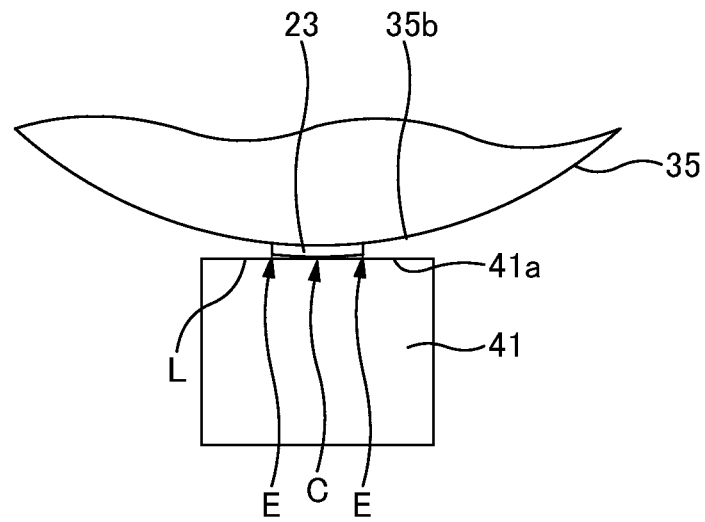
FIG. 8 is a diagram schematically representing the manufacturing apparatus of the related art.

The above matters will be described with reference to FIG. 8 by comparing the absorbent article manufacturing apparatus of the present embodiment and the absorbent article manufacturing apparatus of the related art. FIG. 8 is a diagram corresponding to FIG. 7 and schematically represents the manufacturing apparatus 31 of the related art.

The absorbent article manufacturing apparatus of the related art illustrated in FIG. 8 includes, in a similar manner to the absorbent article manufacturing apparatus of the present embodiment, a lower roll 35 that rotates in a state where the lower roll 35 is opposing a front face 23a of a back-side belt base material 23 that is moving, the lower roll 35 having a peripheral surface 35b that retains a fastening tape member 9, the lower roll 35 causing the fastening tape member 9 to be moved to a position where the fastening tape member 9 is nipped between the front face 23a and the peripheral surface 35b by rotating in a state where the fastening tape member 9 is retained on the peripheral surface 35b; and a hammer roll 41 that bonds the back-side belt base material 23 and the fastening tape member 9 together by coming into contact with a reverse face of the back-side belt base material 23 when the fastening tape member 9 reaches the position and pressing the back-side belt base material 23 towards the peripheral surface 35b. Also, in a similar manner to the absorbent article manufacturing apparatus of the present embodiment, the hammer roll 41 is a roller that is freely rotatable about a central axis, and a central axis direction of the roller intersects with a central axis direction (rotational axis direction of the lower roll 35) of a center of circle of the peripheral surface 35b when the roller comes into contact with the reverse face 23b.

However, the absorbent article manufacturing apparatus of the related art is not configured in such a manner that a line of intersection L of an outer surface 41a of the roller and a virtual plane containing the central axis 41b of the roller being an arcuate curved line, and a diameter of the roller at a central section in the central axis direction of the roller is smaller than a diameter of the roller at an end section of the central axis of the roller. Accordingly, the back-side belt base material 23 and the fastening tape member 9 can be appropriately bonded together. That is to say, with such manufacturing apparatus, the line of intersection L where the outer surface 41a of the roller intersects with the imaginary plane containing the central axis 41b of the roller is a straight line. In such a case, when the hammer roll 41 comes into contact with the reverse face 23b of the back-side belt base material 23 and presses the back-side belt base material 23 towards the peripheral surface 35b, a pressing force exerted on a central section C in a lateral direction (i.e., width direction) of the back-side belt base material 23 and a pressing force exerted on an end section E will be significantly different (in other words, the pressing force on the end section E will be insufficient). Of course, such a situation has an influence on an appropriateness of bonding in bonding the back-side belt base material 23 and the fastening tape member 9 together. In other words, the central section in the lateral direction (i.e., width direction) of the fastening tape member 9 is sufficiently bonded together to the back-side belt base material 23, but the bonding of the end section will be insufficient. If the back-side belt base material 23 and the fastening tape member 9 cannot be appropriately bonded together, there may be a case where one of them will be peeled off from the other.

On the other hand, according to the present embodiment, as shown in FIG. 7, since a line of intersection L of an outer surface 41a of the roller and a virtual plane containing the central axis 41b of the roller is an arcuate curved line, and a diameter of the roller at a central section in the central axis direction of the roller is smaller than a diameter of the roller at an end section of the central axis of the roller, the contour of the outer surface 41a of the roller can be made to lie along a contour of the peripheral surface 35b of the lower roll 35 having a cylindrical shape. Therefore, when the hammer roll 41 comes into contact with the reverse face 23b of the back-side belt base material 23 and presses the back-side belt base material 23 towards the peripheral surface 35b, the pressing force exerted on the central section C in a lateral direction (i.e., width direction) of the back-side belt base material 23 and the pressing force exerted on the end section E becomes even (in other words, the pressing force on the end section E will be sufficient). Therefore, the bonding will be sufficient at both the central section and the end section in the lateral direction (i.e., width direction) of the fastening tape member 9. Accordingly, with the back-side belt base material 23 and the fastening tape member 9 being appropriately bonded together, an occurrence of the above-mentioned peeling off phenomenon will also be appropriately avoided.

Also, in the present embodiment, since the hammer roll 41 comes into contact with a portion on the reverse face 23b of the back-side belt base material 23 where the adhering section 9d (more specifically, the fastening tape member 9 itself) does not exist on the front face 23a side (a vacant portion 23c) and presses the back-side belt base material 23 against the peripheral surface 35b, production of creases can be suppressed when bonding the back-side belt base material 23 and the fastening tape member 9 together.

That is to say, as has been described above, when the hammer roll 41 comes into contact with the above-mentioned reverse face 23b (when the fastening tape member 9 reaches the nipped position), the fastening tape member 9 moves in a direction lying along the central axis direction of the hammer roll 41 and the back-side belt base material 23 is moving in a direction intersecting with the central axis direction. That is to say, the back-side belt base material 23 and the fastening tape member 9 to be bonded together are moving in different directions. Under such condition, assuming that the hammer roll 41 comes into contact with a portion on the reverse face 23b of the back-side belt base material 23 where the adhering section 9d (fastening tape member 9) exists on the front face 23a, there will be a situation in which, at an instant of coming into contact, while the back-side belt base material 23 and the fastening tape member 9 are directly nipped with the hammer roll 41 and the above-mentioned peripheral surface 35b and also pressed (in such a situation, a relative movement of the fastening tape member 9 against the back-side belt base material 23 is not allowed), the back-side belt base material 23 and the fastening tape member 9 moves in a mutually different directions. Such situation causes production of creases.

On the other hand, according to the present embodiment, under a situation where the back-side belt base material 23 and the fastening tape member 9 to be bonded together are moving in different directions, the hammer roll 41 comes into contact with the above-mentioned vacant portion 23c, and therefore, at an instant of coming into contact, the back-side belt base material 23 and the fastening tape member 9 will be not be directly nipped by the hammer roll 41 and the above-mentioned peripheral surface 35b and not pressed, and therefore, some relative movement is allowed for the fastening tape member 9 against the back-side belt base material 23. Then, the slight relative movement will suppress the production of creases.

Also, in the present embodiment, since the hammer roll 41 is a roller that is configured to be freely slidable in the central axis direction, the following advantages can be obtained. That is to say, when the hammer roll 41 comes into contact with the reverse face 23b, the lower roll 35 presses, with its rotation, the hammer roll 41 in the central axis direction of the hammer roll 41 and the hammer roll 41 receives an impact force in the central axis direction from the lower roll 35. In such a case, since the hammer roll 41 slides in the central axis direction, the impact force will be appropriately mitigated.

Other Embodiments

In the above, the absorbent article manufacturing apparatus of the present invention has been described based on the embodiments described above. However, the embodiment of the invention described above is intended to facilitate the understanding of the present invention and not to limit the present invention. It goes without saying that the present invention can be modified or improved without departing from the spirit of the invention and the present invention includes equivalents thereof.

In the embodiment described above, a disposable diaper has been illustrated as an example of an absorbent article, but it is not limited thereto. For example, it may be a sanitary item.

Further, in the present embodiment, the back-side belt base material 23 has been illustrated as an example of a continuous sheet and the fastening tape member 9 has been illustrated as an example of a work, but the continuous sheet and the work are not limited thereto as long as they are constituent elements of the absorbent article. For example, a stomach-side band base material, which is a continuous base material for the above-mentioned stomach-side belt member 3, may be the continuous sheet and the above-mentioned target tape may be the work.

Also, in the present embodiment, the hammer roll 41 is configured to come into contact with a portion on the reverse face 23b of the back-side belt base material 23, specifically a portion where the adhering section 9d (more specifically, the fastening tape member 9 itself, too) does not exist on the front face 23a (vacant portion 23c), but it is not limited thereto. For example, it may be made to come into contact with a portion on the reverse face 23b and specifically to a portion where the fastening tape member 9 exists but the adhering section 9d does not exist. In such a case, production of creases is suppressed as compared to a case where it comes into contact with a portion where the adhering section 9d exists. It is to be noted that the above-mentioned embodiment is more preferable in that production of creases is further suppressed.

Also, in the present embodiment, two hammer rolls 41 are supported by the supporting roller 43 and as a result of the rotation of the supporting roller 43, both hammer rolls 41 come into contact with the back-side belt base material 23 alternately, but it is not limited thereto and a single hammer roll 41 may be supported by the supporting roller 43.

Also, in the present embodiment, the peripheral surface 35b of the lower roll 35 is illustrated as an example of the arcuate retaining surface that retains the work. In other words, an example in which the lower roll 35 itself has a cylindrical shape and the work is retained on this peripheral surface 35b has been illustrated, but it is not limited thereto. For example, the present invention is applicable to an example in which a retaining pallet (see Patent Literature 2 for an example of the retaining pallet) serving as a work retaining member having an arcuate retaining surface is mounted on the rotating member (which may or may not have a cylindrical shape) and the work is retained on this arcuate retaining surface.

Figure 9:
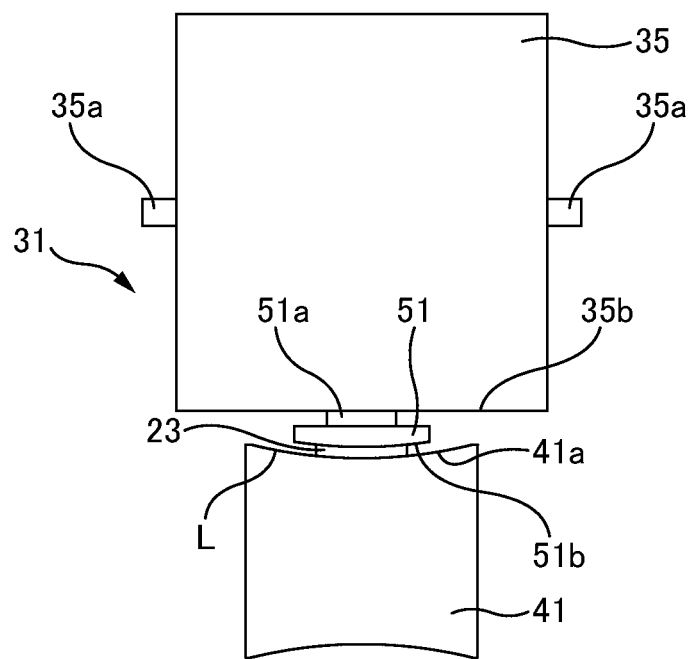
FIG. 9 is a diagram schematically representing the manufacturing apparatus 31 of another embodiment.

Further description will be made with reference to FIG. 9. FIG. 9 is a diagram corresponding to FIG. 7 and schematically represents the manufacturing apparatus 31 of another embodiment. The manufacturing apparatus 31 of the present embodiment includes, similarly to the manufacturing apparatus 31 of the above-mentioned embodiments, a lower roll 35 serving as a rotating member that rotates in a state where the lower roll 35 is opposing a front face of a back-side belt base material 23 that is moving and a hammer roll 41 serving as a pressing member that is freely rotatable about the central axis. The lower roll 35 is provided with a retaining pallet 51 on its peripheral surface 35b via a rotational axis 51a. (It is to be noted that a plurality of the retaining pallets 51 are provided radially in the peripheral direction of the lower roll 35, but FIG. 9 shows only one of the retaining pallets 51 and other retaining pallets are not shown). The retaining pallet 51 is provided with an arcuate retaining surface 51b that retains the fastening tape member.

The lower roll 35 rotates with the fastening tape member being retained on the arcuate retaining surface 51b (in FIG. 9, the rotational axis direction is the left-right direction. A rotational axis 35a is shown in FIG. 9) and moves the fastening tape member to a position at which it is nipped between the front face of the back-side belt base material and the arcuate retaining surface 51b. (It is to be noted that during such movement, the retaining pallet 51 is configured to rotate about the rotational axis 51a and change an orientation of the fastening tape member). The hammer roll 41 bonds the back-side belt base material 23 and the fastening tape member together by coming into contact with the reverse face of the back-side belt base material 23 when the fastening tape member reaches the above-mentioned position and pressing the back-side belt base material 23 towards the arcuate retaining surface 51b.

When the hammer roll 41 (roller) comes into contact with the above-mentioned reverse face, the central axis direction of the roller (in FIG. 9, a left-right direction) intersects with the central axis direction (in FIG. 9, a direction penetrating the plane of paper) of a center of circle of the above-mentioned arcuate retaining surface 51b.

With the configuration of the above-mentioned manufacturing apparatus 31, as shown in FIG. 9, a line of intersection L where the outer surface 41a of the roller intersects with an imaginary plane containing the central axis of the roller is an arcuate curved line and if the radius of the roller at the central section in the central axis direction of the roller is smaller than the radius of the roller at the end section of the central axis of the roller, the above-mentioned effect, i.e., an effect that the back-side belt base material and the fastening tape member can be appropriately bonded together can be achieved.

The invention claimed is:

1. A method of manufacturing an absorbent article, said method comprising:

moving a continuous sheet;

moving a work by a rotating member rotating in a state where the rotating member is opposing a first face of the continuous sheet and has a retaining surface that retains the work thereon while the rotating member is rotated for causing the work to be moved to a position where the work is nipped between the first face and the retaining surface; and bonding the continuous sheet and the work together by a pressing member coming into contact a second face of the continuous sheet when the work reaches the position and pressing the continuous sheet towards the retaining surface, wherein the pressing member includes a roller having a first central axis, the first central axis of the roller is not parallel and not co-planar with a second central axis of the rotating member when the roller comes into contact the second face, the roller of the pressing member has a concave pressing surface, the roller includes a central section and an end section adjacent to the central section along the first central axis of the roller, a diameter of the roller at the central section is smaller than a diameter of the roller at the end section, and when the rotating member retains the work between the first face of the continuous sheet and the retaining surface, the pressing member comes into contact with a portion on the second face of the continuous sheet where the work does not exist on the first face and presses the continuous sheet against the retaining surface.

2. The method according to claim 1, wherein the retaining surface of the rotating member is convex.

3. The method according to claim 1, wherein the roller of the pressing member defines a first roller, and the pressing member further comprises a second roller spaced away from the first roller along the second central axis.

4. The method according to claim 3, wherein, at the bonding, the first roller comes into contact with the second face of the continuous sheet at the portion defining a first portion, and the second roller comes into contact with the second face of the continuous sheet at a second portion, and a dimension of the continuous sheet between the first and second portions is greater than a length of the work along the second central axis of the rotating member.

\* \* \* \* \*